United States Patent
Palander

(12) 
(10) Patent No.: US 6,218,191 B1
(45) Date of Patent: *Apr. 17, 2001

(54) METHOD AND APPARATUS FOR TREATMENT OF HUMAN OR ANIMAL CELL SAMPLES

(75) Inventor: Jari Palander, Mount Waverley (AU)

(73) Assignee: Vision Instruments Limited, Victoria (AU)

( * ) Notice: Subject to any disclaimer, the term of this patent is extended or adjusted under 35 U.S.C. 154(b) by 0 days.

This patent is subject to a terminal disclaimer.

(21) Appl. No.: 09/155,807

(22) PCT Filed: Apr. 11, 1997

(86) PCT No.: PCT/AU97/00228

§ 371 Date: Mar. 2, 1999

§ 102(e) Date: Mar. 2, 1999

(87) PCT Pub. No.: WO97/39328

PCT Pub. Date: Oct. 23, 1997

(30) Foreign Application Priority Data

Apr. 12, 1996 (AU) .................................................. PN 9235

(51) Int. Cl.⁷ ...................................................... G01N 1/28
(52) U.S. Cl. ........................ 436/63; 435/40.5; 435/40.51; 435/288.3; 435/286.3; 435/287.3; 436/46; 422/63; 422/100
(58) Field of Search ............................... 435/40.5, 287.3, 435/40.51, 286.3, 288.3, 305.1, 305.4, 307.1; 356/246; 359/398; 436/174, 176, 63, 46; 422/58, 102, 63, 100

(56) References Cited

U.S. PATENT DOCUMENTS

| | | | |
|---|---|---|---|
| 3,495,926 | * | 2/1970 | Naz . |
| 3,726,764 | | 4/1973 | White . |
| 3,879,106 | * | 4/1975 | McCormick . |
| 3,891,327 | * | 6/1975 | Welch . |
| 5,346,672 | * | 9/1994 | Stapleton . |
| 5,518,925 | | 5/1996 | Tyndorf et al. . |
| 5,538,871 | * | 7/1996 | Nuovo et al. . |
| 5,605,813 | | 2/1997 | Stevens et al. . |
| 5,985,669 | | 11/1999 | Palander . |

* cited by examiner

Primary Examiner—William H. Beisner
(74) Attorney, Agent, or Firm—Pillsbury Winthrop LLP

(57) ABSTRACT

A method for treating a human or animal cell sample (4) arranged on a slide (2) comprises dispensing treatment liquid onto the slide between the sample and the leading edge (5) of a cover tile (1) having a recess or cavity (6). The leading edge is bevelled and has an opening (13) into the cavity. Once dispensing is completed the method involves moving the tile over the slide to trap the liquid in the cavity. A small volume of sealing liquid in the form of evaporation inhibitor liquid, preferably mineral oil, is then applied to the slide preferably at the leading and trailing edges of the tile in a manner causing the evaporation inhibitor liquid to wick around the entire perimeter of the tile to form an airtight seal between the tile and slide around the cavity.

18 Claims, 2 Drawing Sheets

METHOD AND APPARATUS FOR TREATMENT OF HUMAN OR ANIMAL CELL SAMPLES

Figure 1:
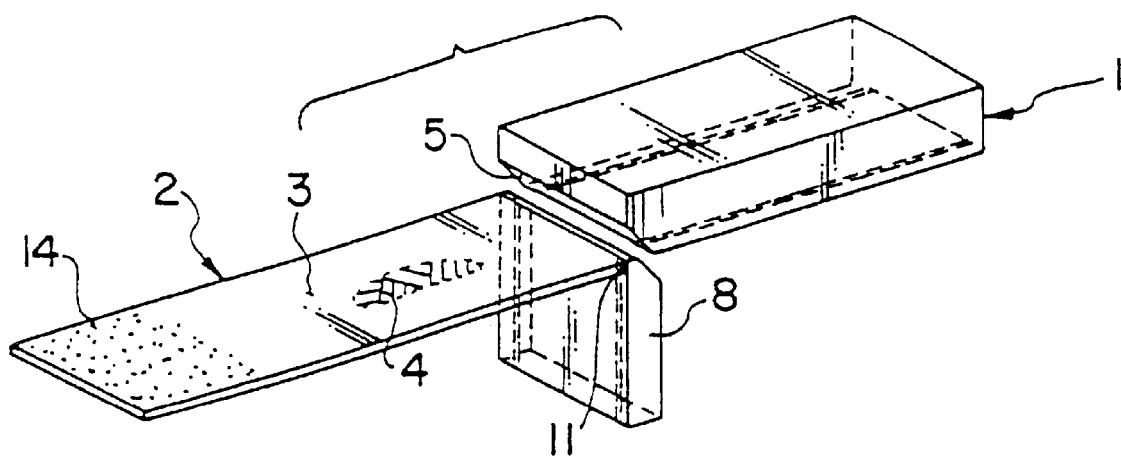

This application is the national phase of international application PCT/AU97/00228 filed Apr. 11, 1997 which designated the U.S.

The present invention relates to a method and apparatus for treatment of human or animal cell samples. In particular, the invention relates to treatment of the samples to enable diagnosis of clinical conditions. A sample is fixed on a flat surface such as a microscope slide and chemically treated with liquid for the purpose of sample hydration or dehydration, or sample staining, or in chemical analysis such as detection of antigens or nucleic acid sequences, for example. The liquids used to treat such sample include:

1. Organic solvents.
2. Antibodies.
3. DNA and RNA probes.
4. Chemical solutions.
5. Washing solutions.

Conventionally the chemical treatment and the chemical analysis of the samples is done by immersing the glass slides on which the samples are fixed into beakers that contain the treatment solutions. Certain treatment liquids are very expensive and are therefore dispensed onto a slide using a pipette with the slide in a horizontal orientation and a glass coverslip is placed on top of the slide to provide spread of the solution and to slow the rate of evaporation of the expensive treatment liquid. The conventional process is labour intensive, exposes workers to reagent fumes and possibly to contact with the chemicals. Accurate timing of the processing steps can also be difficult to achieve. The amount of liquid waste generated is often large, which may be a problem, since the waste that needs to be disposed can contain aggressive solvents or biohazards such as infectious viruses. To overcome some of these problems a number of inventions have been previously proposed for automating the process.

In U.S. Pat. Nos. 4,731,335 and 4,777,020 and 5,002,736 Brigati, D. et al there is described a system where two flat surfaces such as microscope slides are placed face to face with sample sides facing inward. Abutting coating portions of the slides define a capillary gap between the samples. This slide pair can be placed so that the lower edge of the slide pair connects with the treating liquid which will then migrate into the capillary gap. Liquid can then be removed from the gap by placing the slide pair on top of and in contact with absorbent material which will drain and absorb the liquid.

Shandon Scientific Limited U.S. Pat. No. 4,985,206 describes an apparatus for processing tissue. The core of the invention is a channel-defining element. This element is joined together with a slide holding the sample with the sample side facing towards the element. The element forms a channel between its main wall and the slide. When the channel is substantially vertical the upper part of the element forms a liquid dispensing reservoir. An operator or a liquid handling robot is can then fill the reservoir with appropriate reagent. Gravity and capillary action will cause the reagent to migrate into the channel. Once the channel is filled with liquid and the reservoir is empty, the liquid will stay in the gap due to surface tension of the liquid. The liquid in the gap can be replaced by placing new reagent in the reservoir.

Toya, M. et al in U.S. Pat. No. 5,068,091 and UK patent 2,265,981 describes a substantially horizontal wedge shaped capillary gap between a microscopic slide and lower plateau. Liquids can be dispensed to an exposed end of the plateau and capillary action will cause them to migrate to the wedge shaped gap. The gap can then be cleared of the reagent by using suction. Surface tension of the liquid will keep the liquid volume together during the removal process.

The aforementioned prior art apparatus all suffer a disadvantage in that they can in some instances fail to provide an even treatment of the sample with the treating liquid. This is caused by air becoming trapped in the capillary gap. In the case of the Brigati inventions, capillary forces can only lift the liquid a certain distance upwardly from the lower edge of the slide pair and this can lead to a reduced treatment area on the slide. The speed of liquid removal cannot be controlled in the Brigati inventions. The capillary gap also needs to be drained before a new liquid can be applied. These form a disadvantage, because in certain cases it is desirable that the samples are not exposed to air at all when replacing liquids. This is desirable especially when using volatile liquids such as organic solvents that evaporate easily and may let samples dry out during liquid replacement. Sample drying can lead to reduced processing quality such as high non-specific staining. In other cases a film of liquid should be left on the sample to keep it moist during liquid replacement. In the remaining cases it is desirable that the samples are dried completely before applying a new liquid to ensure maximum concentration of the applied liquid.

The apparatus of Shandon has the additional problem that no provision is made for clearing the gap (filling it with air) between different liquid treatments and therefore any air voids trapped in the gap are likely to remain through the process. Also the apparatus of Shandon cannot provide capability to expose the sample to air during processing while liquids are replaced. In the apparatus of Toya M. et al the suction to clear the capillary gap can lead to a breaking-up of the liquid into two or more sections with only one section being sucked into the waste containment system and such an incomplete clearing of the liquid can cause unacceptable treatment of the sample.

Further, the abovementioned prior art all suffer a disadvantage in that the treatment liquid is exposed to the atmosphere and will consequently quickly evaporate, particularly when subjected to heating which is often required for incubation to occur. If the treatment liquid evaporates too quickly the sample will dry out which results in a poor quality treatment or erroneous results.

It has been previously proposed to reduce the rate of evaporation by controlling the humidity of the surrounding atmosphere. This has been most commonly achieved by the use of an electrically heated water bath. However, the level of humidity is difficult to control. Too little humidity can result in the sample drying out and excess humidity can result in condensation forming on the glass slides. This condensation can result in the treatment liquid becoming diluted which lengthens the incubation and can lead to erroneous results. In addition, the condensation forms on surrounding apparatus and chamber walls which make it difficult to observe the process, as well as leading to degradation and corrosion of machine parts. In addition, the warm water in the water bath is a potential source of bacteria and contaminant build up.

Other methods have been proposed for minimizing evaporation, including nail polish or rubber cement to seal coverslip edges onto slides. However, these methods are laborious and difficult to automate. Also, the coverslips are difficult to remove after incubation has been completed since in the first example, acetone is required to remove the nail polish and in the second, the rubber cement must be peeled off manually.

PCT/US91/01108 discloses yet another method of reducing evaporation of a treatment liquid in which an aqueous treatment liquid covering a sample on a glass slide is itself covered by an evaporation inhibitor liquid. This method has the disadvantage that it is not suitable for use with a coverslip since mixing of the treatment liquid and evaporation inhibitor liquid will occur when the coverslip is applied. Further, excessive treatment liquid is required to be applied with this method to ensure an even coverage of the sample by the treatment liquid.

Therefore, it is an object of the present invention to provide a method and apparatus for treating a human or animal cell sample with treatment liquid, in a manner which avoids or at least minimizes evaporation of the treatment liquid.

Accordingly, the invention provides a method of treating a human or animal cell sample with treatment liquid comprising the steps of applying the treatment liquid to a cell sample in a cavity formed between a slide on which the sample is supported and a cover tile placed on the slide, and applying sealing liquid externally of said cavity to seal any air gaps between the cover tile and the slide.

According to a further form of the invention there is provided an apparatus for treating a human or animal cell sample with treatment liquid, said apparatus including means for applying said treatment liquid to the surface of a slide containing said sample, means for placing a cover tile having a recessed face on said slide and over said sample to define said sample, and means for applying a sealing liquid externally of said cavity at a joint between said slide and cover tile to seal any air gaps between the cover tile and the slide.

Figure 2:
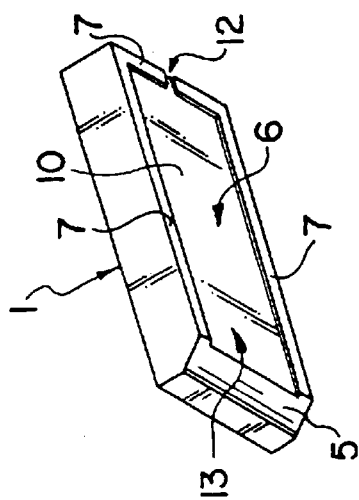
Figure 3:
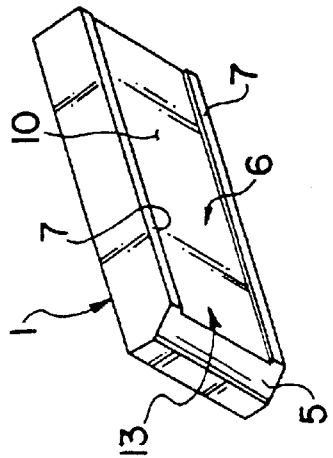
Figure 1A:
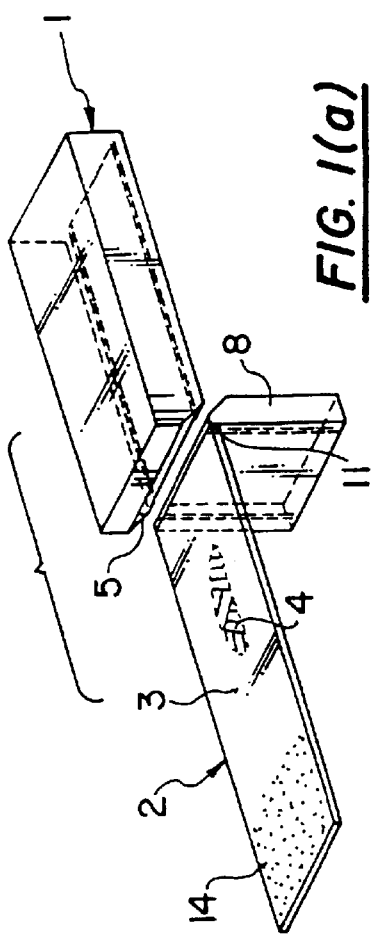
Figure 1B:
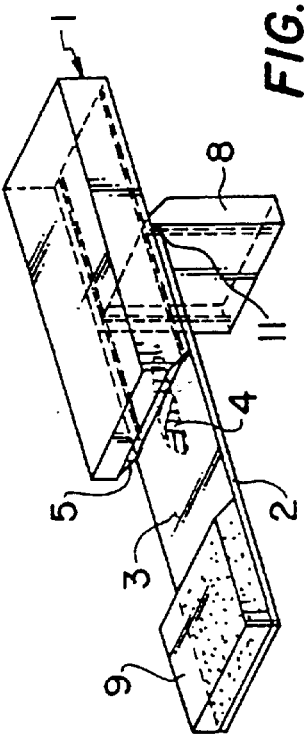
Figure 1C:
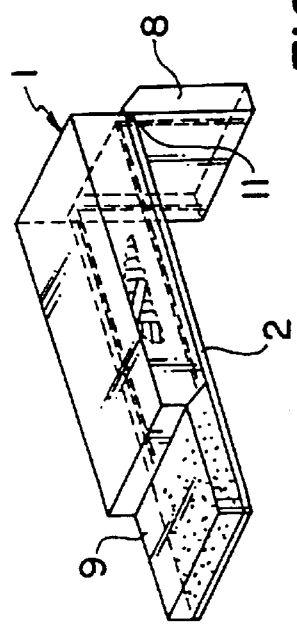

In order that the invention may be more readily understood a particular embodiments will now be described with reference to the accompanying drawings wherein:

FIGS. 1(*a*)–(*c*) shows in three separate views (a), (b) and (c) a perspective of a microscopic slide and associated element of the invention in different relative positions and views (b) and (c) include an end stop on the slide;

FIG. 2 is a perspective underside view of the element of FIG. 1 in one particular form; and FIG. 3 is a similar view to FIG. 2 showing an alternative embodiment of the element.

Referring to FIG. 1, there is shown a cover tile in the form of a substantially flat element 1 and a sample carrying microscopic slide 2. The microscopic slide 2 has a sample carrying or supporting surface 3 on which a sample 4 is to be placed and the flat element 1 has a bevelled edge 5 on one end, defining an opening into a recess or cavity 6 (FIG. 2) formed in a face of the element.

In use, after the sample 4 has been placed on the sample carrying surface 3 of the slide, the flat element 1 and the slide are arranged such that a planar base 10 of the recess 6 and the sample carrying surface 3 are generally parallel to each other with the recess 6 and the sample carrying surface 3 generally facing each other, and such that they are laterally offset from each other with the bevelled edge 5 of the element 1 covering an end portion of the slide 2 adjacent a transverse edge 11 (similar to the position shown in FIG. 1(*a*)). It is preferable, but not essential, that the planar base 10 of the recess 6 and the sample carrying surface 2 are spaced from each other by a distance of about 20 micrometers to 300 micrometers.

The first of a number of treatment liquids (not shown) is then dispensed directly onto the sample 4, or onto the sample carrying surface 3 at a location between the bevelled edge 5 of the element and the sample 4. The element 1 is then moved in a direction towards the sample so that an opening 13 into the recess 6 passes over the sample while the defined distance between the base 10 of the recess 6 and the sample carrying surface 3 is maintained whereby the sample 4 and a major portion of the treatment liquid are trapped within the recess 6.

In some instances, it may be desirable to move the element 1 back and forth on the slide 2 to provide agitation to the liquid before and/or during the incubation process. This agitation can result in a better penetration of the treatment liquid into the sample and thus provide an improved result.

The planar base 10 of the recess 6 is preferably larger than the treated area of the sample 4 carried by the flat surface 3, but smaller than the flat surface itself.

It may be preferable to retain a small amount of the treatment liquid on the sample after the sample has incubated to avoid the sample drying out before the next treatment liquid is applied.

After the sample incubation period has ended, the excess treatment liquid is removed from the sample carrying surface 3 to enable application of the next treatment liquid. This can be done at the same time as the element 1 is retracted along the length of the slide to again expose the sample 4.

As the volume defined between the sample carrying surface 3 and the base 10 diminishes during the reverse movement of the element, that is, as the volume of the recess or cavity 6 decreases, the surface tension of the liquid acts to keep the liquid as a single entity. To remove the excess liquid that does not fit into the diminishing volume, a vacuum nozzle 8 is arranged at the transverse edge 11 of the sample carrying surface 3 such that the nozzle 8 faces the recess 6 and is in close proximity to it. As the element 1 is retracted and moves past the nozzle, the excess treatment liquid is removed from the element 1 by an applied vacuum and is filled into a closed container (not shown) since it could otherwise present an environmental risk. Once the excess liquid for the first treatment has been removed, a second treatment liquid can be dispensed for subsequent incubation, and the process repeated for further treatment liquids as required.

The relative movement of the element 1 and slide 2 can be automated and controlled by a computer (not shown). Since the mechanism does not form part of the present invention it is not considered necessary to describe it herein other than to say that in one form a belt driven linear axis driven by a microstepping step motor is used. Further, this relative movement may be conducted in multiple stages. For example, in the first stage the element may be moved to only partially cover the surface, then halted for a period of time to allow the treatment liquid to fill the space between the bevelled edge 5 of the element 1 and the transverse edge 11 of the slide to minimize the likelihood of air becoming trapped within the recess 6 on completion of the relative movement. In the second stage, the relative movement may be continued again ensuring that any air originally within the recess has been wholly replaced by the sample 4 and the treatment liquid.

Referring now to FIG. 2 which shows one form of the element 1, the recess comprises a substantially flat surface 10 on the element 1 having three outwardly extending protrusions, or rails 7. The rails 7 are arranged in a general "U-shape" which, with the flat base surface 10 on the element 1, defines a recess which is open at one short edge only. This means that in use the recess virtually fully encloses the sample 4. The reason for the recess substantially enclosing the sample 4 is to reduce the evaporation rate of the liquid when trapped in the recess. This is advantageous during prolonged high temperature incubations requiring several treatment processes.

The rail 7 at the other short end of the recess 6 may have a small opening 12 formed in it to allow air to escape from the recess during the relative movement of the element 1 and the slide 2. Alternatively, the rail at the closed end of the recess 6 may be removed altogether as is shown in the alternative embodiment of FIG. 3 to provide an opening 15 into the recess 6 similar to the opening 13 at the other end of the element 1.

In a further alternative, other means may be provided on the element 1 or on the slide 2 to maintain the desired spacing therebetween. Such means could, for example, comprise small bosses or protrusions extending outwardly from the face of the element 1 or from the sample carrying flat surface 3 of the slide 2.

In order to further reduce evaporation of the treatment liquid during incubation, an end stop 9 can be clamped, for example, onto the slide 2 to restrict or close the opening to the recess at the bevelled edge 5 of the element 1. The end stop 9 should be positioned such that it engages the end of the element at the bevel when the element has moved to its final incubation position and for this purpose the end stop 9 has a bevelled edge complimentary to the bevelled edge 5 of the element 1.

Another more preferred method for minimising evaporation of the treatment liquid from the recess or cavity 6 comprises applying a small volume of sealing liquid in the form of an evaporation inhibitor liquid to the element 1 or to the slide 2 at the openings at each end, that is, openings 12 and 13 in FIG. 2 and openings 13 and 15 in FIG. 3. In use, the applied liquid wicks along the openings to trap the treatment liquid within the cavity 6 resulting in minimal subsequent evaporation of the treatment liquid. In fact the sealing liquid tends to wick around the entire perimeter of the element 1 and therefore forms an airtight seal around the cavity 6.

To facilitate automation of the application of the evaporation inhibitor liquid, the glass slide may protrude at each lengthwise end from the element 1 to enable the liquid to be applied directly onto the slide at each end opening. The glass slide 2 may also protrude in a widthwise direction to facilitate application of the liquid at the sides if so desired.

The apparatus for automatically applying the evaporation inhibitor liquid includes a liquid handling robot (not shown) which dispenses the inhibitor liquid at appropriate times in a machine cycle and at appropriate points around the perimeter of the cover tile. The liquid handling robot may also be used to dispense reagents onto slides arranged in a machine (not shown) and for this purpose a series of bottles or vials (not shown) containing the various fluids as well as a bottle for waste s fluid, and a bottle for cleaning fluid, are provided. The machine also includes an air pump (not shown) for a vacuum system, temperature control systems (not shown) and the robot which is an XYZ liquid handling robot in the form of a Cavro RSP9000. The liquids are aspirated into, and dispensed from, a sampling tip on the robot by the action of a syringe pump and various valve mechanisms. A sampling tip wash station is provided to prevent cross contamination between reagents. The use of XYZ robots is common in autosamplers and clinical chemistry analyzers and does not constitute a part of this invention as they are well known in the art.

The machine is constructed to process a large number of slides which are arranged in modules of eight in a row and in one specific form there are six modules in a machine and in another larger machine, there are twelve modules. A tile carriage drive system (also not shown) houses the cover tiles and is driven by a stepper motor for the purpose of moving the respective tiles into position over a slide. Several identical carriage and stepper motor assemblies are included in the machine. The machine may also include a heated water bath as part of a humidity system to control reagent evaporation.

The use of the applied evaporation inhibitor liquid is not to be limited to the specific embodiments of the element 1 described herein as it will wick beyond the end openings and will indeed spread to fill any gap extending around the perimeter of the element 1. The wicking action can be facilitated by moving the element 1 back and forth slightly on the slide 2, but this is not essential. The inhibitor liquid may be applied at one or more points around the perimeter of the element 1 at the joint between the element 1 and the slide 2.

It is preferred when the treatment liquid is aqueous that the evaporation inhibitor liquid is an inert mineral oil. This has an advantage in that it can be readily removed from the element 1 and slide 2 after incubation has been completed using a suitable solvent such as chloroform, acetone, or a chloroform-ethanol mixture.

Ideally, the evaporation inhibitor liquid is inert, is lighter than the treatment liquid, has a boiling point which is higher than the incubation temperature, and has a low viscosity for ease of application. It is also preferable that the evaporation inhibitor liquid is immiscible to avoid any mixing with the treatment liquid. Typical liquids which meet their criteria are hydrocarbons, the most preferred being a mineral oil produced by Molecular Sigma Biology which is branded 'M5904'.

In some instances, it is especially beneficial to the process to add the second or further treatment liquids to the recess 6 without exposing the sample to the air. The reason for this is that exposing the sample to the air may lead to drying of the sample which can reduce the quality of the treatment. This is especially so with some staining procedures.

If air is to be excluded, the current treatment liquid can be replaced by a further treatment liquid by moving the element 1 slightly so that the recess 6 is just open to the vacuum nozzle, then applying vacuum while concurrently dispensing the further treatment liquid onto the sample carrying surface 3. In other words only a small part of the recess or cavity 6 is exposed. It is preferable, in this case, that the further liquid be dispensed at the opposite end of the element to the vacuum nozzle. In practice, the excess of the further treatment liquid tends to migrate to the recess due to the cohesive forces of the liquid while the liquid is under vacuum and will be captured by the vacuum nozzle. The migration of the liquid substantially stops once the excess treatment liquid at the dispensing end is used up.

This process can be facilitated by orienting the whole arrangement at an angle, preferably about 5°, with the vacuum nozzle being at the lower end of the surface and the dispensing of further liquid being at the upper end of the surface.

It is preferable that the element 1 has a thickness which is sufficient to prevent treatment liquids dispensed onto the sample 4 flowing over the top of the element during the relative movement. Typically, this thickness will be more than 2 mm. In addition, the bevelled edge 5 can be angled at various different angles relative to the plane of the surface 3 to allow the element to rise above any obstacles on the slide, for example wax granules on a paraffin fixed sample.

It is preferable that the element 1 be formed of a chemically inert material, so that it does not affect the treatment reactions, and that it be manufactured of a material that withstands organic solvents to allow, for example, dewaxing and dehydration procedures to be conducted on the sample. It is also desirable that the element be manufactured of a transparent or translucent material to enable a user to observe the reaction taking place in the sample. To satisfy all of these requirement the element is preferably formed of glass, and the rails or protrusions are printed or painted onto the element using an inert and durable material such as a Fluoro Ethylene Polymer. Alternatively, the rails may also be formed of glass using various manufacturing processes such as grinding or etching.

If the sample carrying surface is a microscope slide the vacuum nozzle can be placed at the end of the slide that is closest to the sample area. This end is typically opposite to a frosted end 14 of the slide. In a preferred form, the opening of vacuum nozzle can be in the form of slit which may be substantially the same width as that of the microscope slide and it can be aligned such that the slit length is parallel to the face of the microscope slide.

What is claimed is:

1. A method of treating a human or animal cell sample with treatment liquid, comprising:

applying treatment liquid to a cell sample, said cell sample being supported on a slide;

covering the cell sample with a cover tile having a recessed face, said recessed face in combination with said slide defining a cavity comprising said sample; and applying a sealing liquid externally of said cavity to produce an air tight seal between said cover tile and said slide, wherein said cover tile is movable between a first position in which said recessed face is displaced laterally from said sample, and a second position in which said recessed face overlies said sample.

2. A method according to claim 1, wherein the sealing liquid is applied at one or more points around the perimeter of the joint between the slide and the cover tile, and has a low viscosity whereby the sealing liquid wicks along the joint to seal the joint and traps treatment liquid within the cavity.

3. A method according to claim 2, wherein the sealing liquid is an evaporation inhibitor which is inert, lighter than the treatment liquid, and has a boiling point which is higher than an incubation temperature of the sample.

4. A method according to claim 3, wherein the sealing liquid is immiscible with the treatment liquid.

5. A method according to claim 4, wherein the sealing liquid is a hydrocarbon.

6. A method according to claim 5, wherein the sealing liquid is mineral oil.

7. A method according to claim 3, wherein the sealing liquid is a hydrocarbon.

8. A method according to claim 2, wherein said method further comprises moving the cover tile back and forth relative to the slide after application of the sealing liquid to facilitate wicking.

9. A method according to claim 1, wherein the sealing liquid is applied at opposite ends of the cavity.

10. The method of claim 1, wherein said cover tile in combination with said slide defines two openings.

11. The method of claim 10, wherein said openings are defined at opposite ends of said cover tile.

12. The method of claim 11, wherein said cover tile has a rectangular shape.

13. The method of claim 12, wherein said openings are defined at the short ends of said rectangularly shaped cover tile.

14. The method of claim 10, wherein said sealing liquid is applied only at said two openings.

15. Apparatus for treating a human or animal cell sample with treatment liquid, said apparatus comprising a slide containing a sample on a surface thereof, a treatment liquid applicator for depositing treatment liquid onto the surface of said slide containing the sample, a cover tile having a recessed face to extend over said slide and to define a cavity comprising said sample, and a sealing liquid applicator for applying a sealing liquid externally of said cavity along a portion of a joint between said slide and said cover tile to produce an airtight seal between said cover title and said slide, wherein said cover tile is movable between a first position in which said recessed face is displaced laterally from said sample, and a second position in which said recessed face overlies said sample.

16. Apparatus according to claim 15, wherein said apparatus is capable of applying the treatment liquid adjacent an edge of said cover tile before said cover tile is moved from said first position to said second position.

17. Apparatus according to claim 16, wherein said apparatus is capable of moving said cover tile back and forth relative to said slide after application of said sealing liquid.

18. Apparatus according to claim 17, wherein said apparatus is capable of applying the sealing liquid to said slide adjacent opposite open ends of said cavity.

\* \* \* \* \*